US00PP31132P2

(12) United States Plant Patent
Van Swieten

(10) Patent No.: US PP31,132 P2
(45) Date of Patent: Nov. 26, 2019

(54) ***PHALAENOPSIS* ORCHID PLANT NAMED 'PHALGYQXH'**

(50) Latin Name: ***Phalaenopsis* hybrid**
Varietal Denomination: PHALGYQXH

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/350,815

(22) Filed: Jan. 15, 2019

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ..... A01H 5/02; A01H 6/62
See application file for complete search history.

*Primary Examiner* — Annette H Para
(74) *Attorney, Agent, or Firm* — Jondle & Associates, P.C.

(57) ABSTRACT

A new and distinct variety of *Phalaenopsis* plant named 'PHALGYQXH', particularly characterized by having white, flecked and slightly shaded flowers with red-purple lips, 1 to 2 peduncles that are long and sturdy, leaves that are obovate, and is propagated by meristem tissue culture, is disclosed.

3 Drawing Sheets

Genus and species: *Phalaenopsis* hybrid.
Variety denomination: 'PHALGYQXH'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGYQXH'.

The new *Phalaenopsis* plant is a product of a planned breeding program conducted by the inventor in Bleiswijk, The Netherlands. The objective of this breeding program was to create a new *Phalaenopsis* plant with attractive and unique white, flecked, and slightly shaded flowers with red-purple lips, suitable for potted plant production.

The new *Phalaenopsis* plant 'PHALGYQXH' is a result of cross-pollination made by the inventor in June 2009 in Bleiswijk, The Netherlands, of the proprietary female, or seed parent, *Phalaenopsis* hybrid '2526-02' (unpatented) with the proprietary male, or pollen parent, *Phalaenopsis* hybrid '01-3138' (unpatented).

The new *Phalaenopsis* was selected by the inventor as a single plant within the progeny of the stated cross-pollination in a controlled greenhouse in Bleiswijk, The Netherlands, in April 2011. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 24, 2017. 'PHALGYQXH' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands, and can be used to distinguish 'PHALGYQXH' as a new and distinct variety of *Phalaenopsis* plant:

1) White, flecked, and slightly shaded flowers with red-purple lips (intensity and number of flecks may depend on the temperature);
2) 1 to 2 peduncles;
3) Peduncle is long and sturdy; and
4) Shape of the leaf is obovate.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in December 2018. Colors in the photographs may differ from the color values cited in the detailed botanical description, which accurately describe the actual colors of the new variety.

DESCRIPTION OF THE NEW VARIETY

Figure 1:
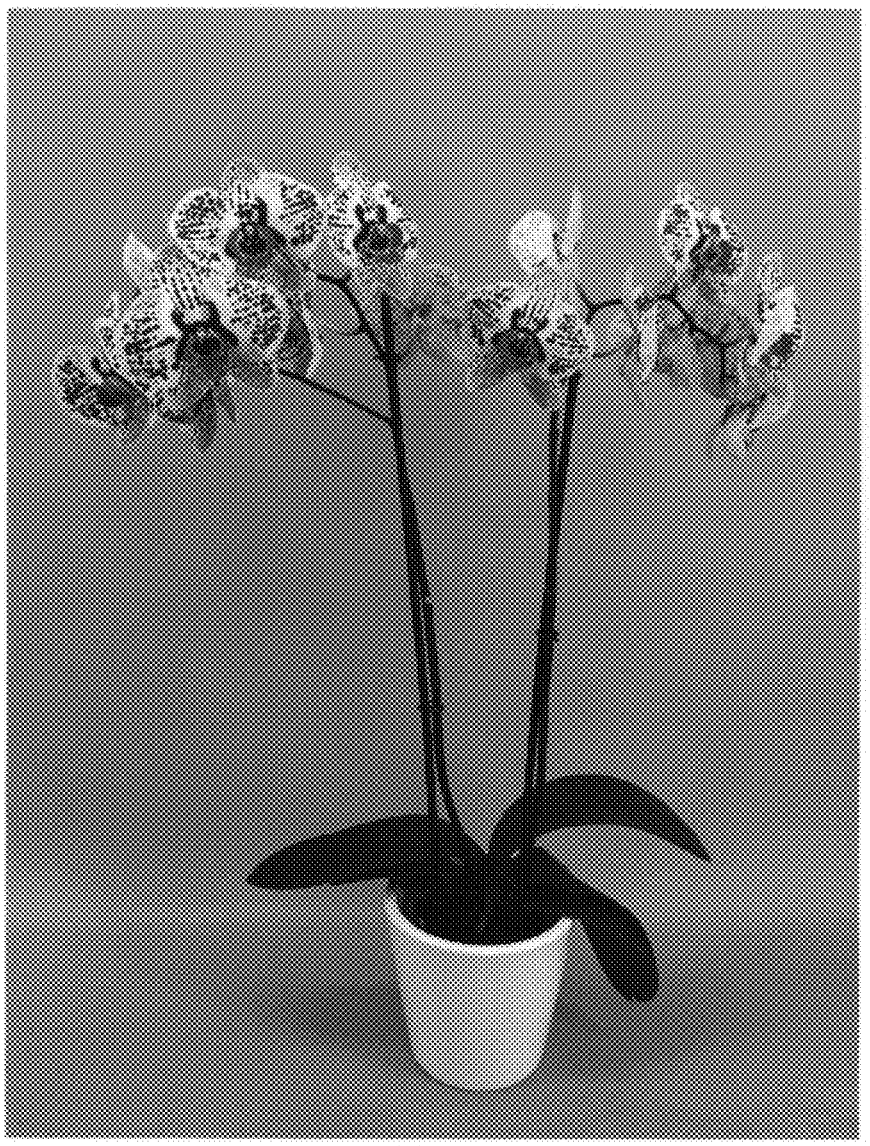
FIG. 1 shows the overall plant habit, including blooms and foliage of 'PHALGYQXH'.
Figure 2:
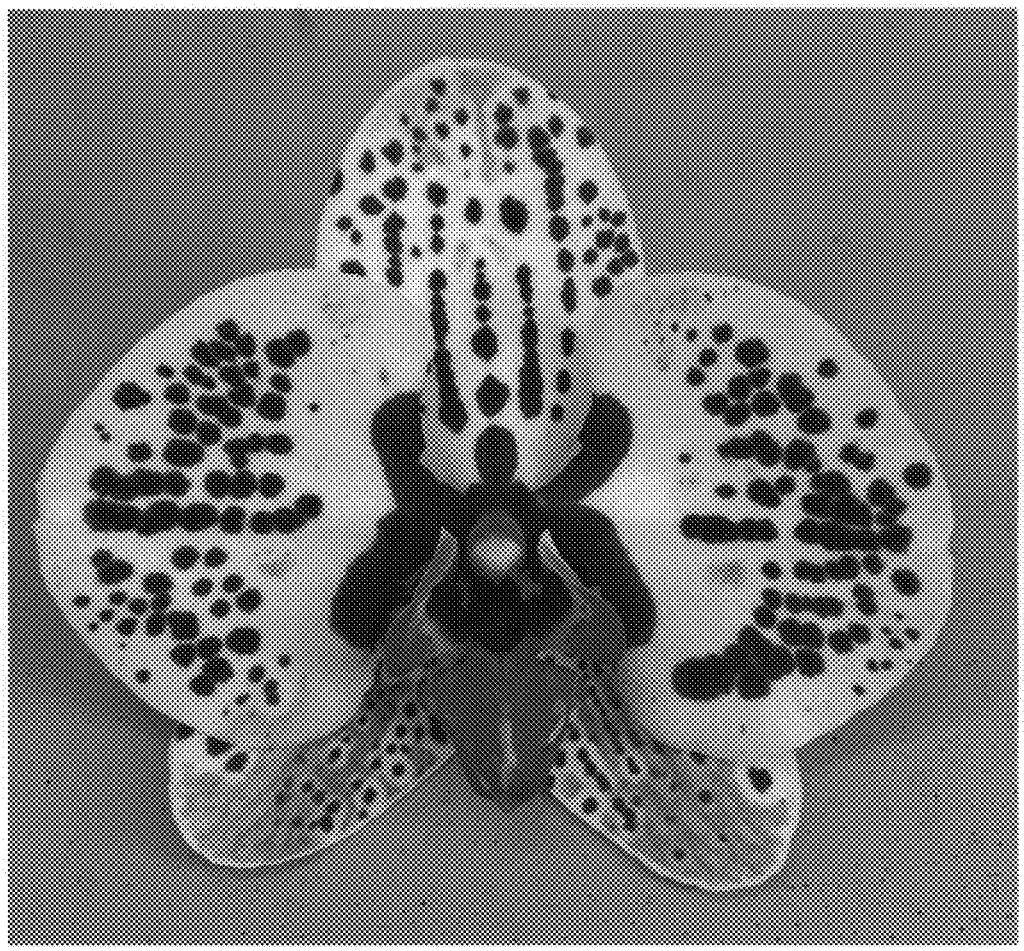
FIG. 2 shows a close-up of a flower of 'PHALGYQXH'.
Figure 3:
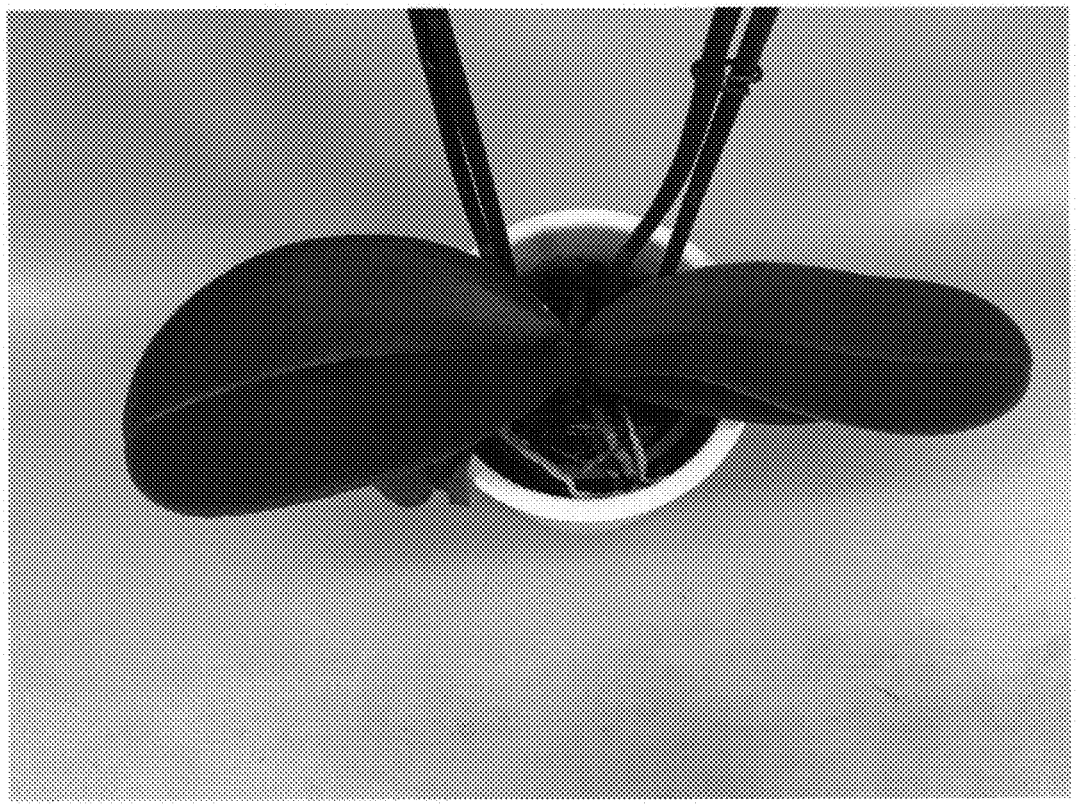
FIG. 3 shows an overhead view of the leaves of 'PHALGYQXH'.

The following detailed description sets forth the distinctive characteristics of 'PHALGYQXH'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in December 2018 on flowering plants which were. planted in 12 centimeter (diameter) pots. After in-vitro propagation, the plants were grown in nursery trays for 20-24 weeks, followed by transplantation to 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12 centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGYQXH'.

Parentage:

*Female parent*.—*Phalaenopsis* cultivar '2526-02' (unpatented).

*Male parent*.—*Phalaenopsis* cultivar '01-3138' (unpatented).

Propagation:

*Type*.—Meristem tissue culture.

Roots:

*Root description*.—Greyed-green (RHS 190B/C) colored roots with branching lateral roots having purplish-red (RHS 187D) colored root tips.

Plant:

*Commercial crop time to flowering*.—Following asexual propagation (in-vitro), the rooted cuttings grow for 20-24 weeks. After transplantation into 12 cm pots, the plants are finished after 48 to 50 weeks.

*Growth habit of peduncle*.—Upright to slightly pendant with raceme to panicle inflorescence.

*Height* (*from soil level to top of inflorescence*).—Approximately 58.0 cm to 63.0 cm.

*Width* (*measured from leaf tips*).—About 38.0 cm to 40.0 cm.

*Vigor*.—Sturdy.

Leaves:

*Mature leaves*.—Quantity per plant: 6 to 8 leaves are produced before flowering. Length (fully expanded): 18.0 cm to 20.0 cm. Width: 8.5 cm to 9.5 cm. Shape: Obovate. Base shape: Moderately elongated. Apex: Rounded unequal. Leaf blade angle with the petiole (measured from the horizontal position): Between 10 degrees and 25 degrees. Leaf margin: Entire. Color: Upper surface: RHS 147A. Lower surface: RHS 146A and diluting dark red (RHS 187A) at the margin. Texture (upper surface): Rough. Thickness: 2.1 mm to 2.6 mm. Venation: Pattern: Parallel. Color of the midvein: Upper surface: RHS 147A. Lower surface: RHS 146A and slightly dark red (RHS 187A) toward the tip.

Peduncle:

*Quantity per plant*.—1 to 2.

*Number of flowers per peduncle*.—8 to 13.

*Length*.—53.0 cm to 58.0 cm.

*Diameter*.—6.0 mm to 6.5 mm.

*Strength*.—Strong.

*Aspect*.—Upright to slightly pendant.

*Texture*.—Smooth.

*Color*.—Brown (RHS 200A).

*Internode length*.—3.0 cm to 5.0 cm.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 190.0 mm to 240.0 mm.

*Flowering time*.—First flowers can be expected 10 to 11 months after planting in a 12 cm (diameter) pot.

*Flower*.—Height: 92.0 mm to 97.0 mm. Diameter: 95.0 mm to 100.0 mm. Depth of lip: 23.0 mm to 25.0 mm.

*Flower longevity*.—On the plant: 9 to 11 weeks.

*Fragrance*.—Absent.

*Flower bud*.—Average size: Large. Length: 29.0 mm to 31.0 mm. Width: 22.0 mm to 24.0 mm. Shape: Egg shaped. Color: Light yellow-green (RHS 145C) with slightly red (RHS 182B) and reddish-purple shade (RHS N78B).

*Petals*.—Arrangement: Open/free. Shape: Semi-circular. Apex: Rounded asymmetric. Margin: Slightly undulated. Length (from base to tip): 45.0 mm to 47.0 mm. Width: 54.0 mm to 56.0 mm. Color (when fully opened): Upper surface: Basic color: White (RHS NN155C). Over color: Dark red-purple flecks (mix of RHS 187B and N79C); slightly purplish-pink shade (RHS N78C). Lower surface: Basic color: White (RHS NN155C). Over color: Diluting dark purplish-red flecks (RHS N79B); slightly light reddish-purple shade (RHS N78D).

*Dorsal sepal*.—Shape: Elliptic. Apex: Rounded to slightly emarginated symmetric. Margin: Entire. Length (from base to tip): 50.0 mm to 52.0 mm. Width: 35.0 mm to 37.0 mm. Color (when fully opened): Upper surface: Basic color: White (RHS NN155C). Over color: Dark red-purple flecks (mix of RHS 187B and N79C); purplish-pink shade (RHS N78C) toward tip. Lower surface: Basic color: White (RHS NN155C). Over color: Diluting dark purplish-red flecks (RHS N79B); slightly light reddish-purple shade (RHS N78D) toward the tip.

*Lateral sepals*.—Shape: Ovate. Apex: Obtuse asymmetric. Margin: Entire. Length (from base to tip): 50.0 mm to 52.0 mm. Width: 28.0 mm to 30.0 mm. Color (when fully opened): Upper surface: Basic color: White (RHS NN155C). Over color: Dark red-purple, flecks (mix of RHS 187B and N79C); purplish-pink shade (RHS N78C) toward tip. Lower surface: Basic color: White (RHS NN155C). Over color: Light yellow-green (RHS 145D) at the base; diluting purplish-red flecks (RHS N79B); light reddish-purple middle vein (RHS N78D) and very light purple (RHS 76B) toward the tip.

*Labellum* (*lip*).—Whiskers: Present. Length of whiskers: 16.0 mm to 18.0 mm. Color of whiskers: Purplish-red (RHS 59B). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated. Length: 19.0 mm to 21.0 mm. Width: 15.0 mm to 17.0 mm. Color: Dark red (RHS 187B) at the base and yellow (RHS 17B) toward base on one side; white (RHS NN155C); red (RHS 185A) toward margin on one side and reddish-purple (RHS N78A) toward other side.

*Apical lobe*.—Shape: Triangular. Margin: Entire. Length: 21.0 mm to 23.0 mm. Width: 18.0 mm to 20.0 mm. Color: Slightly yellow (RHS 17C) and red (RHS 185A) at the base; reddish-purple (RHS N78A) with white middle vein (RHS NN155C) toward whiskers.

*Callus*.—Average size: Medium. Height: 6.0 mm to 7.0 mm. Length: 5.0 mm to 6.0 mm. Width: 4.0 mm to 5.0 mm. Color: Dark red (RHS 187A).

Reproductive organs:

*Column*.—Length: 8.0 mm to 10.0 mm. Diameter: 5.3 mm to 5.8 mm. Color: Light purple (RHS 76B) at the base; reddish-purple (RHS N78B) with white tip (RHS NN155C).

*Pollinia*.—Quantity: 2. Diameter: 1.1 mm to 1.3 mm. Color: Orange (RHS 25A).

*Ovary*.—Length: 10.0 mm to 12.0 mm. Diameter: 2.1 mm to 2.4 mm. Color: Light yellow-green (RHS 144D) and very light purple (RHS 76B) toward the flower.

*Pedicel*.—Length: 36.0 mm to 38.0 mm. Diameter: 2.5 mm to 2.8 mm. Color: Dark purplish-red flecks (RHS N79A) at the base; light yellow-green (RHS 144D) and very light purple (RHS 76B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGYQXH' differs from female parent plant '2526-02' (unpatented) in that 'PHALGYQXH' has flowers with a flecked and shaded pattern and dark red calluses, whereas '2526-02' has flowers with a striped pattern and yellow dotted calluses. Additionally, 'PHALGYQXH' has larger flowers than '2526-02'.

'PHALGYQXH' differs from male parent plant '01-3138' (unpatented) in that 'PHALGYQXH' has flowers with a flecked and shaded pattern, whereas '01-3138' has flowers with a flecked and centered pattern. Additionally, 'PHALGYQXH' has smaller flowers than '01-3138'.

'PHALGYQXH' is most similar to the commercial *Phalaenopsis* plants named 'PHALYDSAP' (U.S. Plant Pat. No. 29,388) and 'PHALFNIWIN' (U.S. Plant Pat. No. 29,629). 'PHALGYQXH' differs from the commercial variety 'PHALYDSAP' in that 'PHALGYQXH' has obovate leaves and rounded to slightly emarginated symmetric dorsal sepal apexes, whereas 'PHALYDSAP' has oblong leaves and obtuse asymmetric dorsal sepal apexes. Additionally, 'PHALGYQXH' has larger flowers and longer whiskers than 'PHALYDSAP'.

'PHALGYQXH' differs from the commercial variety 'PHALFNIWIN' in that 'PHALGYQXH' has flowers with a basic color of white and rounded asymmetric petal apexes, whereas 'PHALFNIWIN' has flowers with a basic color of light purple and emarginated petal apexes.

I claim:

1. A new and distinct variety of *Phalaenopsis* plant named 'PHALGYQXH', substantially as described and illustrated herein.

* * * * *